(12) United States Patent
Kurin et al.

(10) Patent No.: US 8,471,215 B1
(45) Date of Patent: Jun. 25, 2013

(54) INTEGRATED CIRCUIT SAMPLE PREPARATION FOR ALPHA EMISSION MEASUREMENTS

(71) Applicant: Marvell Israel (M.I.S.L) Ltd., Yokneam (IL)

(72) Inventors: Eli Kurin, Zichron Yaakov (IL); Ran Manor, Haifa (IL); Gil Weisman, Kfar Tavor (IL); Yair Faiershtein, Nazareth Illit (IL)

(73) Assignee: Marvell Israel (M.I.S.L) Ltd., Yokneam (IL)

( * ) Notice: Subject to any disclaimer, the term of this patent is extended or adjusted under 35 U.S.C. 154(b) by 0 days.

(21) Appl. No.: 13/707,117

(22) Filed: Dec. 6, 2012

Related U.S. Application Data

(63) Continuation of application No. 12/581,471, filed on Oct. 19, 2009, now Pat. No. 8,330,117.

(60) Provisional application No. 61/150,113, filed on Feb. 5, 2009.

(51) Int. Cl.
*G01T 1/00* (2006.01)

(52) U.S. Cl.
USPC .......................................................... 250/395

(58) Field of Classification Search
USPC .......................................................... 250/395
See application file for complete search history.

(56) References Cited

U.S. PATENT DOCUMENTS

| | | | |
|---|---|---|---|
| 4,680,471 | A | 7/1987 | Morris et al. |
| 2008/0217793 | A1 | 9/2008 | Choudhary et al. |

*Primary Examiner* — David Porta
*Assistant Examiner* — Hugh H Maupin

(57) ABSTRACT

Test samples for use in conducting integrated circuit alpha particle emissions testing, processes for preparing test samples for use in conducting integrated circuit alpha particle emissions testing, and processes for conducting integrated circuit alpha particle emissions testing using the test samples, are described. The approach takes into account the effects of the relative physical positions of the respective components within a final integrated circuit package, and takes into account the effect of contamination of individual components or of the integrated circuit package as a whole due to conditions and/or processes performed during the production process. The described approach relates to test sample preparation and integrated circuit alpha particle emissions testing for integrated circuits in which the alpha particle emission levels are extremely low, i.e., in the ultra low alpha region, for example, alpha particle emissions less than 0.002 cph/cm$^2$.

17 Claims, 5 Drawing Sheets

INTEGRATED CIRCUIT SAMPLE PREPARATION FOR ALPHA EMISSION MEASUREMENTS

INCORPORATION BY REFERENCE

This application is a divisional of U.S. patent application Ser. No. 12/581,471, filed on Oct. 19, 2009, which claims the benefit of U.S. Provisional Application No. 61/150,113, "A METHOD FOR INTEGRATED CIRCUIT (IC) SAMPLE PREPARATION FOR ALPHA EMISSION MEASUREMENTS," filed by Eli Kurin, Ran Manor, Gil Weisman and Yair Faiershtein on Feb. 5, 2009, the disclosure of each of which is incorporated herein by reference in their entireties.

BACKGROUND

An alpha particle is a nucleus of helium (He), emitted during radioactive decay. Materials used to produce integrated circuits and integrated circuit packages and materials/contaminants inadvertently included in integrated circuits and integrated circuit packages during a manufacturing process on a specific production line may contain radioactive substances that emit alpha particles via radioactive decay. Examples of such radioactive materials include, but are not limited to, uranium impurities, thorium impurities (and their daughter products), and lead isotope Pb-210. These substances are capable of emitting alpha particles at parts per million (PPM) and parts per billion (PPB) levels. The kinetic energy of an emitted alpha particle is in the 4-9 MeV (million electron-volts) range. An emitted alpha particle can travel a distance of several centimeters, e.g., 2-7 cm, through air and can travel a distance of tens of microns, e.g., 20-100 µm, in silicon (SI).

With the ongoing dimension shrinkage of modern integrated circuits, transistor dimensions and transistor threshold voltages have been greatly reduced. As a result, modern integrated circuits with reduced dimensions have become increasingly sensitive to alpha radiation. For example, the radiation energy of alpha particles imparted to an integrated circuit transistor can cause an internal data state upset, e.g., a switch from a HIGH state to a LOW state, or vice versa, by generation of electrons and holes. Amongst the most vulnerable structures are those of high density transistor memories such as, for example, double data rate dynamic random access memory (DDR DRAM), double data rate synchronous dynamic random access memory (DDR SDRAM), as well as various flip-flop (FF) structures.

A data bit upset caused by impact of an alpha particle emission on a transistor within an integrated circuit does not cause physical damage to the transistor or to the integrated circuit. Further, the data bit upset, or data bit error, is recoverable using commonly used data processing techniques, such as data interleaving as well as data refresh. For this reason, such data bit errors are called soft errors. A soft error rate (SER) is the rate at which an integrated circuit is predicted to encounter soft errors. A soft error rate for a device can be expressed as either number of failures-in-time (FIT), or mean-time-between-failures (MTBF).

The background description provided herein is for the purpose of generally presenting the context of the disclosure. Work of the presently named inventors, to the extent the work is described in this background section, as well as aspects of the description that may not otherwise qualify as prior art at the time of filing, are neither expressly nor impliedly admitted as prior art against the present disclosure.

SUMMARY

In accordance with an embodiment of the disclosure, alpha particle measurements are performed on test samples obtained from a final product, integrated circuit package specimens retrieved from a known production line. In an example embodiment, a method for IC sample preparation for accurate measurement of alpha emission rate is described, whereby undesired package components are removed so that the region of interest (ROI), i.e., the region corresponding to those portions of the package that emit alpha particles which can affect operation of electronic components, e.g., transistors, on the silicon die, is carefully exposed without alpha contamination during the sample preparation process.

In one example embodiment, a method for measuring alpha emissions in a circuit package is described that includes, attaching a silicon die to a substrate of the circuit package, encapsulating at least one surface of the substrate with a low emission encapsulating material, said encapsulation covering an area that is larger than the silicon die, removing the silicon die from the circuit package, and measuring alpha emissions from the circuit package.

In a second example embodiment, a method of preparing a test sample for alpha emissions testing is described that includes, retrieving an integrated circuit package from a production line, the retrieved integrated circuit package having a layered structure that includes, a package substrate, a silicon die having an integrated circuit, solder bumps connecting the silicon die to the package substrate, and an underfill material positioned between the silicon die and the package substrate, removing the silicon die from the layered structure, and encapsulating at least one surface of the package substrate with an a low alpha particle emitting encapsulating material.

In a third example embodiment, an alpha particle emissions test component extracted from an integrated circuit package is described that includes, a layered structure extracted from the integrated circuit package that includes, a package substrate of the integrated circuit package, solder bumps that, in the circuit package, connect a silicon die to the package substrate, and an underfill material that, in the integrated circuit package, was positioned between the silicon die of the integrated circuit package and the package substrate, the underfill material exposed by grinding away the silicon die, and an encapsulation material that covers a surface of the package substrate not covered by one of the solder bumps and the underfill material.

In one or more additional embodiments, the method for measuring alpha emissions in a circuit package further includes, determining a soft error rate for the circuit package based on the measured alpha emissions. Further, in one or more embodiments of the method for measuring alpha emissions in a circuit package, encapsulating further includes encapsulating edges of the substrate with an encapsulation material, such as an underfill material. In addition, in one or more additional embodiments of the method for measuring alpha emissions in a circuit package, removing the silicon die further includes polishing the silicon die to remove the silicon die from the circuit package to expose flip chip bumps and underfill, etching the silicon die to remove the silicon die from the circuit package to expose flip chip bumps and underfill, milling the silicon die to remove the silicon die from the circuit package to expose flip chip bumps and underfill, or grinding the silicon die to remove the silicon die from the circuit package to expose flip chip bumps and underfill.

BRIEF DESCRIPTION OF THE DRAWINGS

Example embodiments of a test sample for use in conducting integrated circuit alpha particle emissions testing and a process for preparing the test sample will be described with reference to the following drawings, wherein like numerals designate like elements, and wherein.

DETAILED DESCRIPTION OF EMBODIMENTS

The described embodiments relate to integrated circuit test sample preparation and integrated circuit alpha particle emissions testing for integrated circuits in which the alpha particle emission levels are extremely low, i.e., in the ultra low alpha (ULA) region, for example, alpha particle emissions less than 0.002 count-per-hour/centimeter$^2$ (cph/cm$^2$). Example embodiments of an integrated circuit test sample for use in conducting integrated circuit alpha particle emissions testing, example embodiments of a process for preparing integrated circuit test samples for use in conducting integrated circuit alpha particle emissions testing, and example embodiments of a process for conducting integrated circuit alpha particle emissions testing of integrated circuits based on the described integrated circuit test sample embodiments, are described. The described approach takes into account the effects of production processes, e.g., on a specific fabrication or assembly production line, on the alpha particle content of individual components or of the integrated circuit device as a whole.

Figure 1:
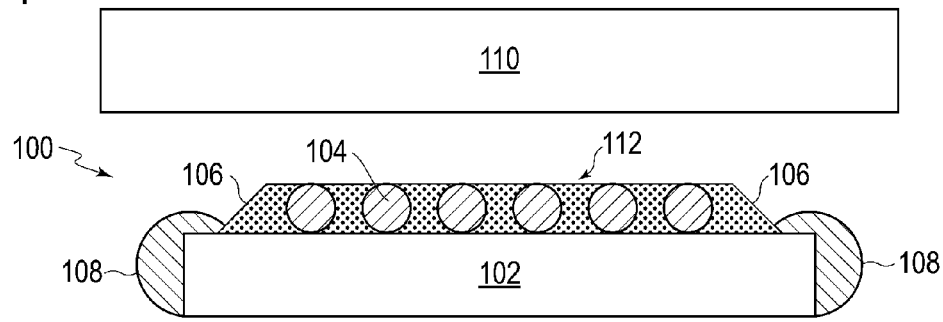
FIG. 1 is a block diagram of an alpha particle emissions test configuration that includes a prepared integrated circuit test sample and an alpha particle detection unit.

FIG. 1 is a block diagram of an alpha particle emissions test configuration. As seen in FIG. 1, the alpha particle emissions test configuration includes an alpha particle detector 110 and a test sample 100. During the alpha emissions test process, alpha particle detector 110 is placed in close proximity to test sample 100 to obtain a count of alpha particles emitted from test sample 100 over time.

Alpha emissions are capable of traveling approximately 2-7 cm through air, but are capable of traveling only much shorter distance through solid materials. Therefore, to produce a test sample 100 that is capable of producing, in the test configuration at alpha particle detector 110, a count of alpha particles representative of the number of alpha particles that would impact a silicon die mounted to top surface 112 of the underfill layer of test sample 100, portions of an integrated circuit package are removed and other portions of the integrated circuit package are encapsulated.

For example, as described in greater detail below with respect to FIG. 2 through FIG. 6, test sample 100 shown in FIG. 1 may be extracted from a finished integrated circuit package produced, for example, on an integrated circuit package production line. Portions of the integrated circuit package, that are not sufficiently proximate to the silicon die within the integrated circuit package configuration to affect, by alpha particles radiation, operation of electronic components on the silicon die are removed, or encapsulated, to prevent alpha particle detector 110 from generating an erroneous count of alpha particles. Further, portions of the integrated circuit package that would block alpha particles generated by other portions of interest of the integrated circuit package that are sufficiently proximate to the silicon die within the integrated circuit package configuration to affect operation of electronic components on the silicon die are also removed to prevent an erroneous alpha particle count by alpha particle detector 110.

As seen in FIG. 1, and as described further with respect to FIG. 2 through FIG. 6, test sample 100 may retain only a small portion of the original integrated circuit package, i.e., those portions that are capable of emitting alpha particles that can affect operation of electronic components operating on the silicon die. For example, from the original integrated circuit package described below with respect to FIG. 2, example test sample 100 retains only package substrate 102, solder bumps 104, and underfill material 106. Portions of package substrate 102 that remain exposed but that are not sufficiently close to the silicon die in the integrated circuit package to affect operation of electronic components on the silicon die with alpha emissions are shielded using edge encapsulating material 108. For example, edge encapsulating material 108 may be an ultra low alpha particle emitting epoxy of sufficient thickness to hold/retain alpha particles emitted from the edges of package substrate 102 so that alpha particles emitted from the edges of package substrate 102 do not impinge on the particle detector 110. It is noted that the portions of the integrated circuit package that are retained in any given test sample 100 can vary based on the type and the configuration of the respective integrated circuit package from which it is produced. It is noted that the package substrate material is a relatively large emitter of alpha particles and therefore, if not properly shielded the unshielded package substrate material will result in erroneous alpha readings by the particle detector 110.

Figure 2:
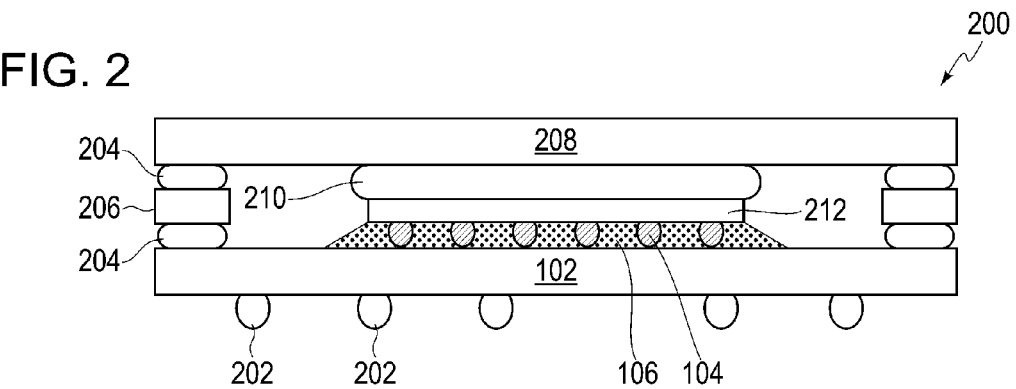
FIG. 2 is a schematic diagram of an example complete flip-chip integrated circuit package including an integrated circuit and all components included in the example flip-chip integrated circuit package.

FIG. 2 is a schematic diagram of an example integrated circuit package that uses a controlled collapse chip connection, or flip-chip, configuration. As seen in FIG. 2, an example flip-chip integrated circuit package 200, includes a package substrate 102, solder bumps 104, underfill material 106, solder balls 202, adhesive 204, a stiffener ring 206, a heat slug lid 208, thermal interface material 210 and a silicon die 212.

A flip-chip silicon die 212 is an integrated circuit in which solder bumps 104 are plated or printed. The flip chip silicon die 212 is mounted and electrically connected to an opposite side of substrate 102 pads by re-melting solder bumps 104. After silicon die 212 has been mounted to substrate 102, underfill material 106 typically is injected to fill air-gaps between silicon die 212 and substrate 102 and to affix silicon die 212 more securely to substrate 102. In one example embodiment, underfill material 106 may be an ultra low alpha emission epoxy that shields silicon die 212 from alpha particles emitted from substrate 102. In an embodiment, a top portion of the flip-chip integrated circuit package 200 includes heat slug lid 208 and thermal interface material 210 that work together to efficiently transfer heat from the silicon die 212 to air or external heat sink. In an embodiment, side portions of flip-chip integrated circuit package 200 include stiffener ring 206 which is mounted between heat slug lid 208 and substrate 102 with adhesive 204.

Figure 3:
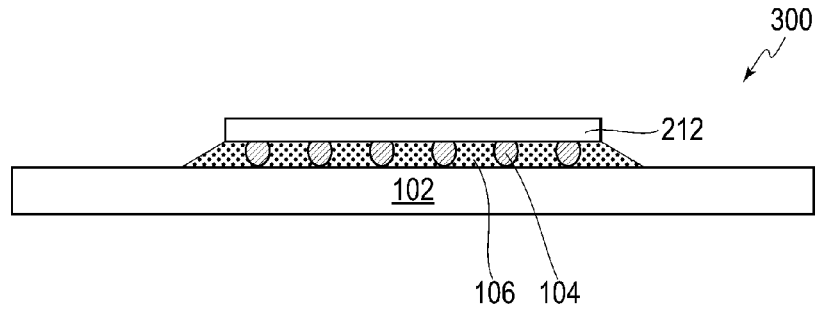
FIG. 3 is a schematic diagram of the flip-chip integrated circuit package of FIG. 2, in which selected top and side components have been removed.

FIG. 3 is a schematic diagram of the flip-chip integrated circuit package of FIG. 2, in which solder balls 202, adhesive 204, stiffener ring 206, heat slug lid 208, and thermal interface material 210 have been removed.

For example, solder balls 202, adhesive 204, stiffener ring 206 are removed, in part, because they are not sufficiently proximate to the silicon die within the integrated circuit package configuration to affect operation of electronic components, including e.g. transistors, disposed on the silicon die. If not removed, however, these same components could emit alpha particles that may be detected by alpha particle detector 110 resulting in an erroneous count of alpha particles, since a portion of the detected particles included in the count would not affect operation of electronic components disposed on the silicon die.

Heat slug lid 208 and thermal interface material 210 are removed from the package because any alpha particles emitted by heat slug lid 208 and thermal interface material 210 within a flip-chip integrated circuit package are blocked from affecting operation of electronic components on silicon die 212 by the silicon substrate of silicon die 212. Further, heat slug lid 208 and thermal interface material 210 are removed because they are located in positions within the integrated circuit package that would tend to block alpha particles generated by other portions of the integrated circuit package that are included in the test sample 100 from being counted by alpha particle detector 110.

Figure 4:
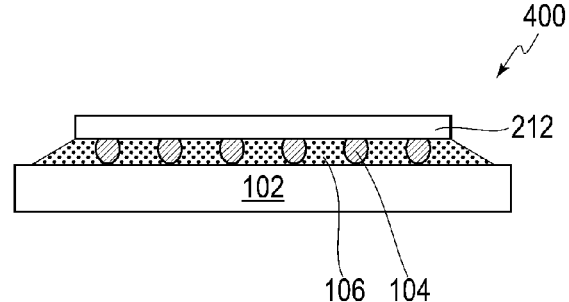
FIG. 4 is a schematic diagram of the altered flip-chip integrated circuit package of FIG. 3, in which a portion of the package substrate has been removed.

FIG. 4 is a schematic diagram of the altered flip-chip integrated circuit package of FIG. 3, in which outer portions of package substrate 102 have been removed with a cutting device such as a precision saw blade, laser cutter, dicing machine, etc., to so that the dimensions of package substrate 102 are slightly larger than the dimensions of silicon die 212.

The outer portions of package substrate 102 are removed, in part, because they are not sufficiently proximate to the position of a silicon die within the integrated circuit package configuration to affect operation of electronic components on the silicon die. If not removed, however, these same outer portions of package substrate 102 could emit alpha particles that may be detected by alpha particle detector 110 resulting in an erroneous count of alpha particles.

Figure 5:
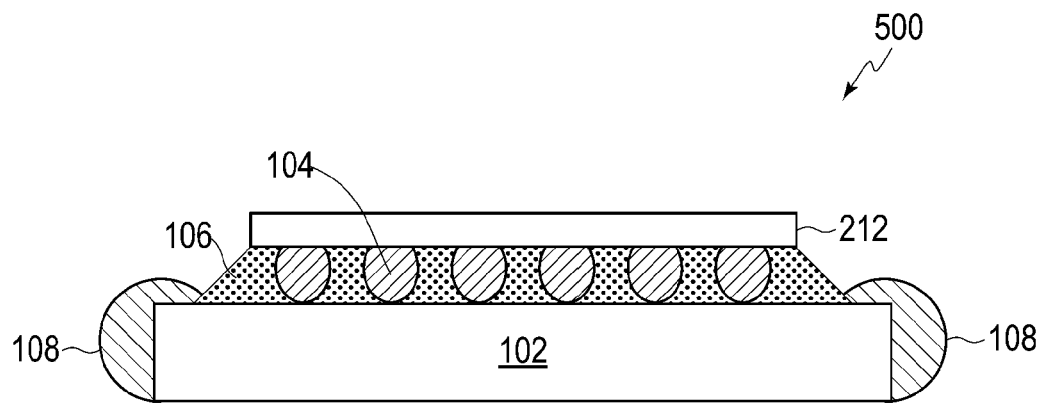
FIG. 5 is a schematic diagram of the altered flip-chip integrated circuit package of FIG. 4, in which exposed surfaces of the package substrate have been covered with an encapsulating material.

FIG. 5 is a schematic diagram of the altered flip-chip integrated circuit package of FIG. 4, in which exposed surfaces of the package substrate have been covered with an encapsulating material 108.

The outer edges of package substrate 102 are encapsulated, in part, because they are not sufficiently proximate to the position of a silicon die within the integrated circuit package configuration to affect operation of electronic components on the silicon die. If not removed, however, these outer edges of package substrate 102 could emit alpha particles that may be detected by alpha particle detector 110 resulting in an erroneous count of alpha particles that includes alpha particles that are not expected to affect operation of electronic components on the silicon die.

In one example embodiment, the surface and edges of package substrate 102 are encapsulated with an ultra low alpha emission epoxy. For example, in one example embodiment, the encapsulating material may be the same, or similar, to underfill material 106 that fills the gaps between silicon die 212 and package substrate 102. However, any suitable low alpha emission encapsulating material of sufficient thickness to block alpha particles emitted from the top surface and/or sides of package substrate 102 may be used.

Encapsulating material 108 may be applied to test sample 100 in any manner, such as dipping a portion of test sample 100 into encapsulating material 108 while encapsulating material 108 is in a liquid form and allowing encapsulating material 108 to harden, or brushing encapsulating material 108 onto desired portions of test sample 100 while encapsulating material 108 is in a liquid form and allowing encapsulating material 108 to harden. In any case, encapsulating material 108, e.g., ultra low alpha emission encapsulating material 108, should cover the side edges of package substrate 102 and should cover the surface of package substrate 102, that will face towards alpha particle detector 110 during testing, up to silicon die 212 and/or up to underfill material 106, as seen in FIG. 5 and FIG. 6.

Figure 6:
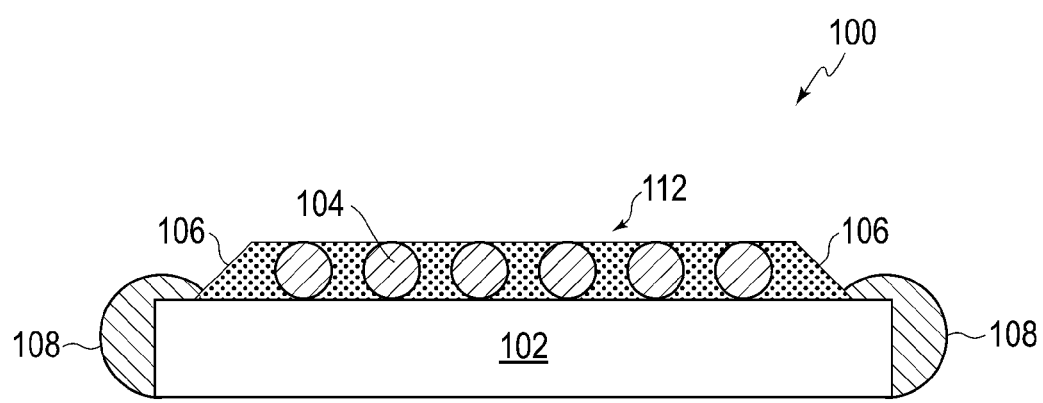
FIG. 6 is a schematic diagram of the altered flip-chip integrated circuit package of FIG. 5, in which the silicon die has been removed.

FIG. 6 is a schematic diagram of the altered flip-chip integrated circuit package of FIG. 5, in which the silicon die has been removed resulting in the production of a final test sample 100, as first described above with respect to FIG. 1.

Silicon die 212 is removed so that alpha particles emitted by underfill material 106 and solder bumps 104 can impact alpha particle detector 110 during testing. If the silicon die 212 were not removed, alpha particles emitted by underfill material 106 and solder bumps 104 would impact and be blocked by silicon die 212, resulting in an erroneous count of alpha particles by alpha particle detector 110.

In an example embodiment, silicon die 212 is removed using one or more of any number of removal techniques, such as grinding and/or polishing away silicon die 212 using a grinding/polishing surface, such a diamond lapping film; milling away silicon die 212 using a milling machine; and/or etching away silicon die 212 using a suitable dry silicon etching technique, and/or a wet silicon etching technique that does not leave alpha particle emitting residues.

Figure 7:
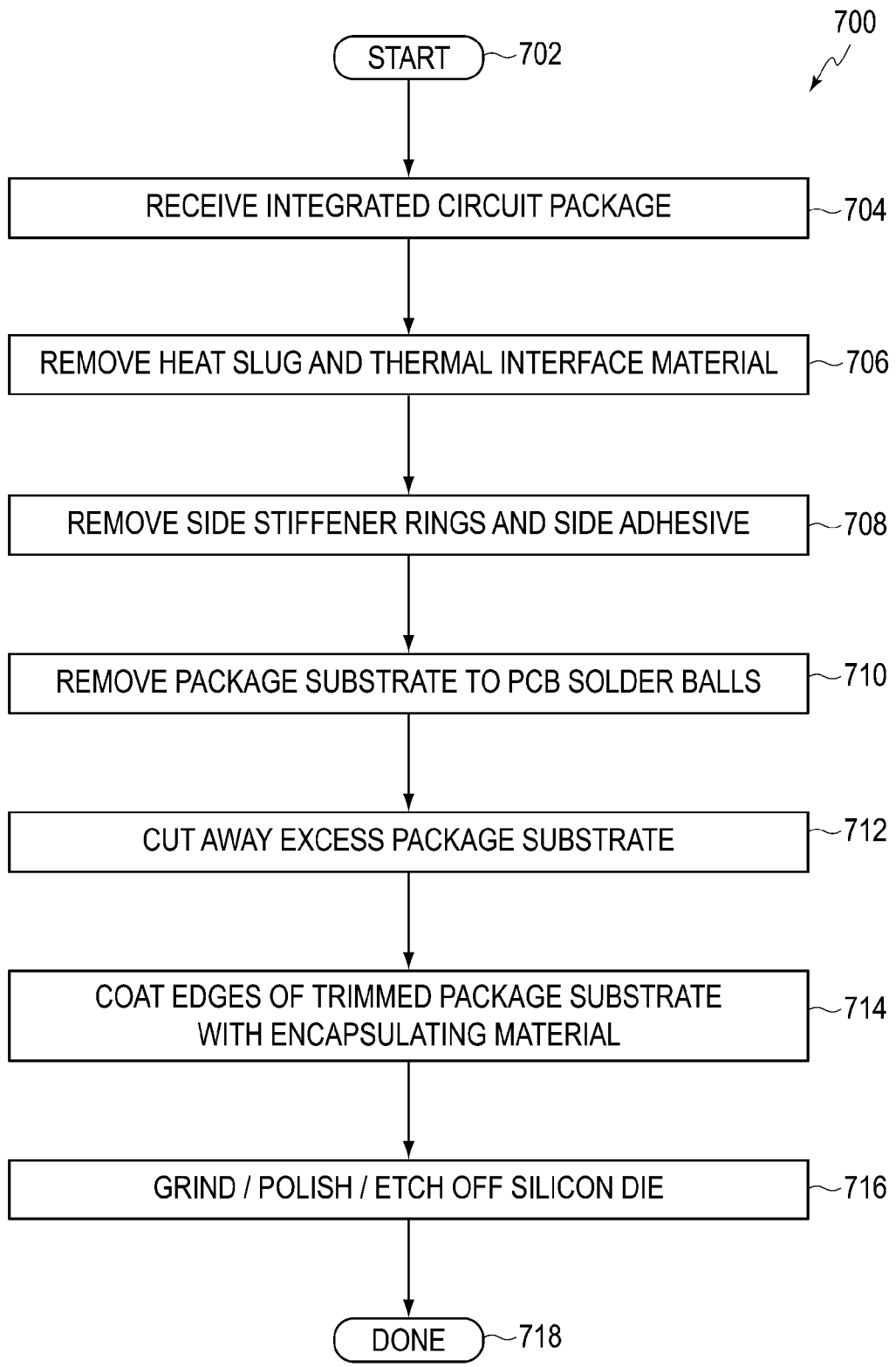
FIG. 7 is a flow-chart of an example process flow that may be performed to prepare an example test sample, as shown in FIG. 1, from an example integrated circuit package.

FIG. 7 is a flow-chart of an example process flow for preparing an example test sample, as described above with respect to FIG. 1 and FIG. 6, from an example integrated circuit package. It is assumed in the process flow described below with respect to FIG. 7 that the integrated circuit package from which the test sample is prepared is based on a flip-chip design such as that described with respect to FIG. 2, above. However, the process flow described below with respect to FIG. 7 may be modified to produce a test sample that is suitable for alpha emission testing from any integrated circuit package configuration by, for example, removing and/or encapsulating corresponding components in a manner similar to that described above with respect to FIG. 2 through FIG. 6 and below with respect to FIG. 7 for an integrated circuit package not based on a flip-chip design.

For example, a test sample 100 suitable for alpha particle emission testing can be made from any integrated circuit package by removing, or encapsulating, those portions of the integrated circuit package that are not sufficiently proximate to the silicon die within the integrated circuit package configuration to affect operation of electronic components on the silicon dies, and by removing those portions of the integrated circuit package that would block alpha particles generated by other portions of the integrated circuit package that are sufficiently proximate to the silicon die within the integrated circuit package configuration to affect operation of electronic components on the silicon die, as described above. As seen in FIG. 7, operation of process 700 begins at S702 and proceeds to S704.

At S704, an integrated circuit package is received from a selected integrated circuit package production line, and operation of the process continues at S706.

At S706, a top portion of the integrated circuit package, which in the case of a flip-chip integrated circuit package typically includes, as seen in FIG. 2, heat slug lid 208 and thermal interface material 210, is removed to expose the silicon die within the circuit package, and operation of the process continues at S708.

At S708, vertical side portions of the integrated circuit package, which in the case of a flip-chip integrated circuit package typically includes, as seen in FIG. 2, side stiffener ring 206 and adhesive 204, are removed to expose the outer edges of package substrate 102, and operation of the process continues at S710.

At S710, portions of the integrated circuit package attached to package substrate 102 on a side opposite silicon die 212 are removed which, in the case of a flip-chip integrated circuit package, typically includes, as seen in FIG. 2, solder balls 202, to expose a clean outer surface of package substrate 102, and operation of the process continues at S712.

At S712, selected portions of package substrate 102 which extend past edges of silicon die 212 mounted to one side of package substrate 102 and/or which extend past underfill material 106, are removed, e.g., by cutting through package substrate 102 with a device such as a precision saw blade, laser cutter or dicing machine, etc., to reduce the dimensions of package substrate 102 to roughly match the dimensions of silicon die 212, and operation of the process continues at S714.

At S714, faces of trimmed package substrate 102 which extend past the edges of the silicon die 212 and/or underfill material 106 are encapsulated with an encapsulating material, e.g., an ultra low alpha emission encapsulating material, and operation of the process continues at S716.

It is noted that, at S714, any exposed face of trimmed package substrate 102 should be encapsulated to prevent alpha particles emitted from an un-encapsulated face of trimmed package substrate 102 from being detected by alpha particle detector 110, thereby causing alpha particle detector 110 to generate an erroneous count of alpha particles over time.

At S716, silicon die 212 is removed from the integrated circuit package using, for example, grinding, etching, and/or polishing techniques, as described above with respect to FIG. 6 to expose a surface 112, which in the case of a flip-chip integrated circuit package may include, as shown in FIG. 1 and FIG. 6 an upper surface of bumps 104 and underfill material 106, and operation of the process terminates at S718.

A test sample 100 produced in a manner described above with respect to FIG. 7 from an integrated circuit package manufactured on a production line that produces such integrated circuit packages for actual use, takes into account the effects of the relationships of the respective components within a final integrated circuit package, and takes into account the affect of possible contamination of individual components or of the integrated circuit package as a whole due to conditions and/or processes performed during the production process on that production line. Therefore, the described approach provides a more accurate alpha particle emission count than would be achieved, for example, based on an analysis of discrete components used to manufacture the integrated circuit device. In this way of sample preparation the measured alpha particles corresponds to an actual alpha flux to which the silicon integrated circuit is exposed.

Figure 8:
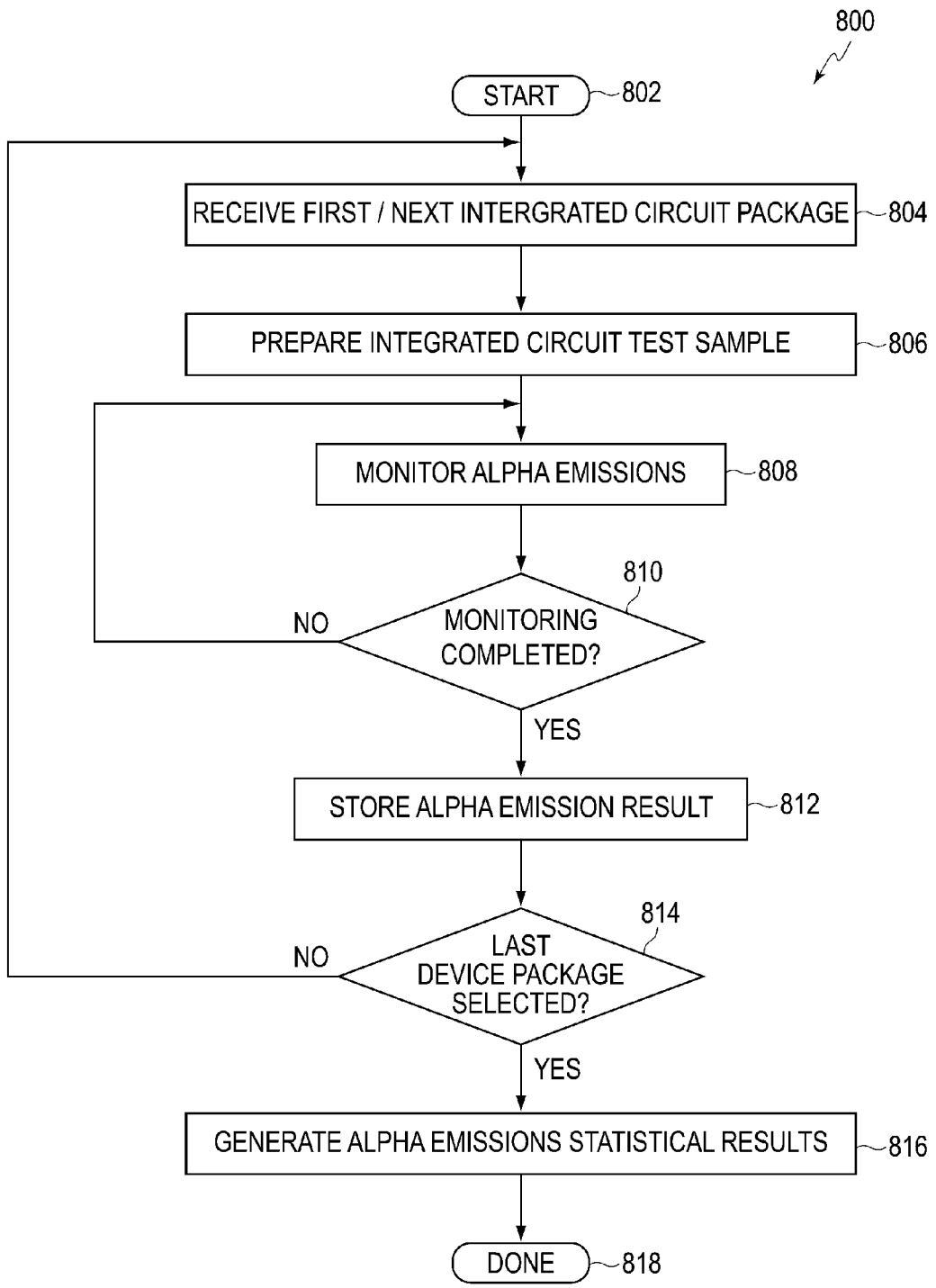
FIG. 8 is a flow-chart of an example process flow that may be used to perform integrated circuit package alpha particle emissions testing.

FIG. 8 is a flow-chart of an example process flow that may be used to perform alpha particle emissions testing of an integrated circuit package to obtain an accurate measure of alpha particle emissions capable of affecting operation of electronic components within the integrated circuit of the integrated circuit package. The alpha particle emission measurements may be used to produce accurate estimates of the soft error rate that may be experienced by the integrated circuit as a result of alpha emissions. As seen in FIG. 8, operation of process 800 begins at S802 and proceeds to S804.

At S804, a first/next integrated circuit package is received from a selected integrated circuit package production line, and operation of the process continues at S806.

At S806, a test sample is prepared from the received integrated circuit package using, for example, the process described above with respect to FIG. 7, and operation of the process continues at S808.

At S808, the test sample is placed in an alpha particle emissions test configuration, such as that described above with respect to FIG. 1, alpha particle emissions from the test sample are monitored and counted over time, and operation of the process continues at S810.

At S810, once a stable and accurate counting of alpha particle has been achieved and the gathered data is statically to a high level of confidence, operation of the process continues at S812; otherwise, operation of the process continues at S808.

At S812, the alpha particle emissions count over time recorded by alpha particle detector for the test sample is stored, and operation of the process continues at S814.

If, at S814, a last integrated circuit package has been tested and recorded, operation of the process continues at S816; otherwise, operation of the process continues at S804.

At S816, the alpha emission results generated for the respective test samples produced from a common type of integrated circuit package, e.g., an integrated circuit package produced on a common production line, are processed to produce alpha emissions statistical results for the integrated circuit package. For example, such statistics may include a mean rate of alpha emissions, an average standard deviation from the mean for the test samples tested, and/or additional statistics that may include or exclude specific test samples with an alpha emission result that lies outside the statistical norm. Further, a soft error rate and/or mean time between failures may be determined for integrated circuit packages based on the generated alpha emissions statistical results, and operation of the process terminates at S818.

Figure 9:
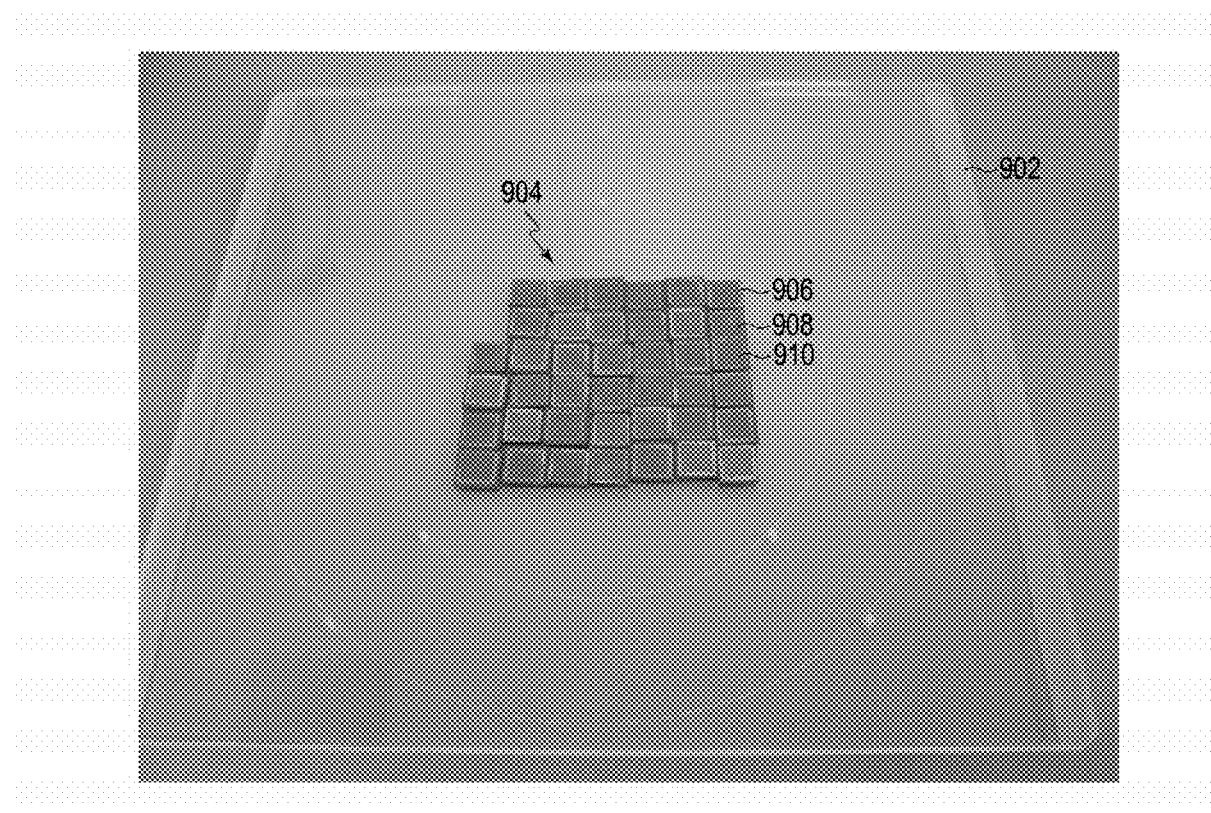
FIG. 9 is a photograph of multiple example test samples arranged in a group for placement in an alpha particle emissions test configuration, as shown in FIG. 1, for alpha particle emissions testing as a group.

FIG. 9 is a photograph of multiple example test samples arranged in a group for placement in an alpha particle emissions test configuration, as shown in FIG. 1, for alpha particle emissions testing as a group. As shown in FIG. 9, test samples, e.g., test sample 906, test sample 908, and test sample 910, can be arranged in a group 904 on a low alpha particle emitting tray 902, in preparation for placement under an alpha particle detector in an alpha particle emissions test configuration, as shown in FIG. 1. With respect to process from described above with respect to FIG. 8, the group of test samples shown in FIG. 9 may treated as a single test sample. Grouping the test samples is such a manner expedites alpha emissions testing by reducing the time required to achieve a stable and accurate count of alpha particles emitted over time.

Using such an approach, the alpha emissions particle count generated by the alpha particle detector is a cumulative alpha particle count for all the test samples included in the group over the monitored time period. Dividing the resulting cumulative alpha particle count by the sum of the cumulative exposed alpha particle emitting surface area, e.g., in centimeters squared ($cm^2$), of the test samples included in the group provides an average alpha particle count per unit of surface area, e.g. $cm^2$. Dividing the average alpha particle count per unit of surface area, e.g., $cm^2$, by the duration of the monitoring period, e.g., hours (hr), provides an average alpha particle count for a standard unit time for a standard unit of area, e.g., a count per hour per centimeter squared ($cph/cm^2$).

For purposes of explanation in the above description, numerous specific details are set forth in order to provide a thorough understanding of the described test sample for use in conducting integrated circuit alpha particle emissions testing, the described process for preparing test samples for use in conducting integrated circuit alpha particle emissions testing, and the described process for conducting integrated circuit alpha particle emissions testing of integrated circuits based on the described test sample embodiments. It will be apparent, however, to one skilled in the art that the described embodiments may be practiced without these specific details. In other instances, various structures and devices are omitted from the figures, or are depicted in simplified and shown in block diagram form, in order to avoid obscuring the teaching features of the described embodiments.

While the test sample for use in conducting integrated circuit alpha particle emissions testing, the process for preparing test samples for use in conducting integrated circuit alpha particle emissions testing, and the process for conducting integrated circuit alpha particle emissions testing of integrated circuits based on the test sample embodiments, have been described in conjunction with the specific embodiments thereof, it is evident that many alternatives, modifications, and variations will be apparent to those skilled in the art. Accordingly, the described embodiments, as set forth herein, are intended to be illustrative, not limiting. There are changes that may be made without departing from the spirit and scope of the invention.

What is claimed is:

1. An alpha particle emissions test component extracted from an integrated circuit package, comprising:
    a layered structure extracted from the integrated circuit package, the layered structure comprising:
        a package substrate of the integrated circuit package;
        solder bumps that, in the circuit package, connect a silicon die to the package substrate; and
        an underfill material that, in the integrated circuit package, positioned between the silicon die of the integrated circuit package and the package substrate, the underfill material exposed by removing the silicon die from the layered structure; and
    an encapsulation material that covers a surface of the package substrate not covered by one of the solder bumps and the underfill material.

2. The alpha particle emissions test component of claim 1, wherein the encapsulation material, solder bumps, and the underfill material cover a surface area that is greater than a surface area of the silicon die.

3. The alpha particle emissions test component of claim 1, wherein a count of alpha particles emitted from the layered structure in absence of the silicon die that is removed is obtained by an alpha particle detector.

4. The alpha particle emissions test component of claim 3, wherein the silicon die is removed from the layered structure to expose the underfill material by one of polishing, etching, milling, and grinding the silicon die.

5. The alpha particle emissions test component of claim 3, wherein the count of alpha particles is used to produce estimates of a soft error rate caused by alpha emissions.

6. The alpha particle emissions test component of claim 1, wherein the encapsulation material encapsulates at least one surface of the substrate with a low emission encapsulating material.

7. The alpha particle emissions test component of claim 6, wherein the low emission encapsulating material is an ultra low alpha particle emitting epoxy that retains alpha particles emitted from the at least one surface of the substrate.

8. The alpha particle emissions test component of claim 1, wherein the encapsulation material is configured to shield edges of the substrate.

9. The alpha particle emissions test component of claim 8, wherein, before removal of the silicon die from the layered structure, the edges of the substrate are not close enough to the silicon die to affect operation of electronic components on the silicon die with alpha emissions.

10. A method for measuring alpha emissions in an integrated circuit package, comprising:
    extracting a layered structure from the integrated circuit package;
    connecting a silicon die by solder bumps to a package substrate of the layered structure;
    positioning an underfill material between the silicon die and the package substrate;
    removing the silicon die from the layered structure to expose the underfill material;
    covering a surface of the package substrate not covered by one of the solder bumps and the underfill material by an encapsulation material; and
    obtaining a count of alpha particles emitted from the layered structure in absence of the silicon die by an alpha particle detector.

11. The method of claim 10, further comprising:
    covering a surface area that is greater than a surface area of the silicon die by the encapsulation material, solder bumps, and the underfill material.

12. The method of claim 10, wherein removing the silicon die from the layered structure is achieved by one of polishing, etching, milling, and grinding the silicon die.

13. The method of claim 10, further comprising:
    producing, from the count of alpha particles, estimates of a soft error rate caused by alpha emissions.

14. The method of claim 10, further comprising:
    encapsulating at least one surface of the substrate with a low emission encapsulating material.

15. The method of claim 14, wherein the low emission encapsulating material is an ultra low alpha particle emitting epoxy that retains alpha particles emitted from the at least one surface of the substrate.

16. The method of claim 11, further comprising:
    shielding edges of the substrate.

17. The method of claim 16, further comprising:
    forming the edges of the substrate not close enough to the silicon die to affect operation of electronic components on the silicon die with alpha emissions.

* * * * *